(12) United States Patent
Grech

(10) Patent No.: US 8,354,118 B2
(45) Date of Patent: Jan. 15, 2013

(54) METHODS FOR CONTROLLING MOLLUSCS

(75) Inventor: Nigel M. Grech, Fresno, CA (US)

(73) Assignee: Sci Protek, Inc., Visalia, CA (US)

( * ) Notice: Subject to any disclaimer, the term of this patent is extended or adjusted under 35 U.S.C. 154(b) by 560 days.

(21) Appl. No.: 12/500,489

(22) Filed: Jul. 9, 2009

(65) Prior Publication Data

US 2009/0274646 A1    Nov. 5, 2009

Related U.S. Application Data

(62) Division of application No. 10/871,195, filed on Jun. 18, 2004, now Pat. No. 7,566,461.

(51) Int. Cl.
*A01N 25/32* (2006.01)
*A01N 25/12* (2006.01)

(52) U.S. Cl. .......... 424/406; 424/84; 424/405; 424/410

(58) Field of Classification Search .................. None
See application file for complete search history.

(56) References Cited

U.S. PATENT DOCUMENTS

| | | | |
|---|---|---|---|
| 4,765,979 A | | 8/1988 | Nielsen |
| 4,906,653 A | | 3/1990 | Kiehs et al. |
| 5,135,744 A | | 8/1992 | Alexander et al. |
| 5,207,389 A | | 5/1993 | Hall |
| 5,246,936 A | * | 9/1993 | Treacy et al. ............ 514/256 |
| 5,290,557 A | | 3/1994 | Mason et al. |
| 5,362,749 A | | 11/1994 | Henderson et al. |
| 5,437,870 A | | 8/1995 | Puritch et al. |
| 5,527,525 A | | 6/1996 | Wilson |
| 6,093,416 A | | 7/2000 | Young |
| 6,136,340 A | | 10/2000 | Chuhran |
| 6,479,062 B2 | | 11/2002 | Vander Hooven |
| 6,565,860 B1 | | 5/2003 | Walker |
| 6,682,755 B1 | | 1/2004 | Chuhran |
| 2005/0118225 A1 | | 6/2005 | Wirth |
| 2005/0163815 A1 | | 7/2005 | Bowen et al. |

FOREIGN PATENT DOCUMENTS

| | | |
|---|---|---|
| WO | WO9222205 | 12/1992 |
| WO | WO00/15033 | 3/2000 |
| WO | WO03067982 | 8/2003 |
| WO | WO03092385 | 11/2003 |
| WO | WO03092386 | 11/2003 |

OTHER PUBLICATIONS

Brandt, Jr., et al., Evaluation of Alfalfa-Corn Cob Associative Action. I. Interactions between Alfalfa Hay and Ruminal Escape Protein on Growth of Lambs and Steers, J. Anim. Sci. 1986. 63:894-901.
Baalawy, S. S., "Relative Effectiveness of Corncobs and Polyester Granules as Vehicles for Bayluscide", Bulletin of the World Health Organization, vol. 35, No. 3, p. 451, 1966.
Ma, An-Ning, et al., "Preliminary report on the role of plant granules for trapping snails and slugs", Hu-Pei University Journal, Natural Science, vol. 25, No. 3, pp. 260-262, Sep. 2003.
Ma, An-Ning, et al., "Preliminary report on the role of plant granules for trapping snails and slugs", Hu-Pei University Journal, Natural Science, vol. 25, No. 3, pp. 260-262, Sep. 2003. (English Translation).
Smith, et al.—New Baits and Attractants for Slugs, J. of Economic Entomology 63(6) 1970, pp. 1919-1922.
Slug & Snail Pests in Agriculture, 1996, UK, 41 pgs.
Office Action dated Jul. 15, 2011—EP Application 05 757 706.6-1219.

* cited by examiner

Primary Examiner — Neil Levy
(74) Attorney, Agent, or Firm — Mark D. Miller

(57) ABSTRACT

Novel materials for controlling molluscs, such as snails and slugs, using carbohydrates including celluloses, hemicellulose complexes, and/or lignin, for inducing death in molluscs. The materials are non-toxic, will not contaminate a drinking water supply, will not harm fish, birds or wild life, will not cause any harmful effects if swallowed or absorbed through the skin, will not harm children or pets, and can be safely eaten by domestic animals and livestock that may consume such dead molluscs. The materials may be applied in various formulations at various water contents. The materials do not provide nutrition to the molluscs, and disrupt normal bodily functions resulting in death. An attractant may be included to encourage ingestion by the molluscs.

18 Claims, No Drawings

METHODS FOR CONTROLLING MOLLUSCS

This is a divisional of U.S. patent application Ser. No. 10/871,195 filed on Jun. 18, 2004 which is incorporated herein in its entirety by this reference.

BACKGROUND OF THE INVENTION

The present invention relates to methods and materials for killing molluscs by exposing them (either by ingestion and or skin contact) to an effective amount of a molluscicide made of structural carbohydrates such as plant derived celluloses, hemi-celluloses and lingo-celluloses.

FIELD OF THE INVENTION

Numerous products are available for controlling molluscs such as slugs and snails. The majority of them rely on metabolic poisons for their effect. Although effective, an undesirable consequence of their inherent toxicity is the possibility of non-target toxicity. Indeed every year in the United States pets, wildlife and children are unfortunately exposed to these poisons.

Such products usually employ an inert substance combined with a metabolic poison. Traditional approaches to mollusc control rely heavily on toxic chemicals such as methiocarb and metaldehyde. Molluscicide formulations based on these two materials constitute the vast majority of control methods for molluscs globally. High toxicity is inherent in their composition and non-target species effects are very serious. Thus, products containing a toxicant (i.e., a poisonous additive or chemical such as methiocarb and metaldehyde) may only be used in carefully selected areas to avoid contaminating food supplies, water supplies, domestic animals and people.

Conventional molluscicides are undesirable because other animals such as birds, mammals and reptiles feeding on these products (or indeed feeding on the poisoned mollusks), may also die from these toxic products. Dogs are particularly susceptible to certain chemical molluscicides such as metaldehyde. Chemically based molluscicides may also have a major impact on beneficial organisms found in the same ecological niches as slugs and snails, such as earthworms and insects. Concerns of this sort have led to the withdrawal of some molluscicides such as methiocarb from the California market.

As with many other areas of pesticide research there is a continued endeavor to discover new technologies that are safer to non-target species and the environment. Some of these are based on simple metal salts and/or enhancing agents. In addition, compounds to increase the repellency of toxic molluscicides to non-target species such as dog, cats and humans, are routinely used.

Previously it has been discovered that certain carbohydrates from certain plants may be used to control rodents and insects, as described in U.S. Pat. Nos. 6,136,340 and 6,682,755. The present invention describes the lethal effect of these materials on molluscs, a new and previously unknown effect.

SUMMARY OF THE INVENTION

The present invention relates to the discovery that structural plant carbohydrates can kill molluscs when administered to them, preferably by ingestion. Plant structural carbohydrates are mainly composed of celluloses, lignocellulose complexes and/or hemicelluloses. Such plant derived structural carbohydrates include, for example, but are not limited to corn cob, hay, straw, seed husks, seed chaff, spent grain, bagasse, sugar beet pulp, coconut coir fiber, sisal fiber, hemp, coconut shells, peanut shells, cotton fibers, rice hulls, plant stalks, and other plant fibers in various forms but not limited to crushed, milled, powdered, granulated and pelletized preparations.

Important in the mechanism of action for the invention described herein is the encouragement of continued feeding in the target mollusc pest (the purpose of the attractant). The result of this continued feeding over several days will be to prevent normal gut function such as the absorption of digested food components from the mollusc gut, osmoregulation, and normal water retention. The interruption of these necessary bodily functions eventually results in death of the mollusc.

In one embodiment of the invention, the structural carbohydrate (SC) material is rich in cellulose and/or hemi-celluloses and/or lignin and used for controlling molluscs without using a conventional toxic component. The material preferentially includes an active ingredient and an attractant/binder. The molluscs receive no nourishment from the structural carbohydrates. Their metabolism is disrupted and dehydration occurs. Additionally the invention described herein induces massive intestinal dysfunction leading to the impairment of normal mollusc digestive tract absorption and osmoregulation. Water loss from the gut is exacerbated by this invention due to its tendency to be extremely hydrophilic and absorb many times its own mass in water. Additional disruptive physiological effects caused by the ingestion of compositions according to the invention include without limitation reduced food intake, bleaching, reduced feces production, reduced movement, weight loss, increased dormancy, reduced reproductive activity and increased mortality.

Contact between the structural carbohydrates and the external surfaces of the mollusc causes water loss from the mollusc tissues. Sufficient exposure can result in dehydration and death of the mollusc.

Examples of formulae for the product include the following:

| Material | Percentage | Purpose |
| --- | --- | --- |
| Structural carbohydrates | 10-99% | Active Ingredient |
| Molasses | 1-25% | Attractant/Binder |
| Plant oils | 0.001-5% | Attractant |
| Polymers | 0.01-3% | Anti weathering agent |
| Acid/base | 0.1-0.5% | pH stabilizer |

Examples of structural carbohydrates include plant derived materials such as but not limited to: corn cob, cereal stalks, cereal seed husks and hulls, nut shells, cereal seed chaff, legume seed pods, peanut shells, plant fiber (e.g., cotton and wood), sugar beet and sugar cane bagasse, hops, sisal fiber, bran, beet pulp, hay, and straw hemp, among others. Synthetically produced structural carbohydrates may also be used.

Molasses is used as an attractant/binder because, as with other attractants, it also provides binding capability. For example, cane molasses is used extensively in the baking industry as a shortening agent. It improves the flavor, provides cohesion and improves the "texture" of the foodstuff. Thus, molasses or other similar materials may be used as agents to improve the consistency, cohesiveness, and texture of the preferred molluscicide, as well as to improve the palatability of the invention to molluscs.

Examples of plant oils include fats and oils, such as peanut oil, soybean oil, cottonseed oil, corn oil, vegetable oil, coconut oil, lard, tallow, nut butter (e.g., peanut). Oils are used extensively as shortening; in salad oils, livestock feed, soaps, paints and lubricants. Proteins can also be used as attractants, for example dried milk. Glutens are proteins derived from grains; used in the preparation of foods, especially cereals; used in cattle feed and in making adhesives. The purpose of the oils, fats, proteins and/or glutens is to act as an attractant, i.e., a substance used to attract pests such as molluscs to the bait. The purpose of the attractant is to overcome "bait shyness" and encourage the consumption of the molluscicide by the molluscs. Some simple sugars, complex carbohydrates, and proteins that may be used include: maple sugar, beet molasses, cottonseed meal, cane molasses, cane syrup, honey, corn syrup, bone meal, malt sugar and beer/ales, among others.

Cane molasses is used extensively in baked goods and candies and is a major raw material for livestock feed and as a binder. Cane syrup and corn syrup are used extensively in baked goods and candies as binders. High protein products such as milk and blood products can be used to enhance the attractiveness of the bait to the various species of molluscs.

Using corn as an example, the corn plant is actually a grass and the kernels themselves are grains. The fiber in corn seed structures is mostly insoluble; yet, in oats and barley (which are also cereals, as is corn) seed structures, the fiber is mostly soluble. Fiber found in the stalks of all cereals is largely insoluble. The fiber in corn seed structures passes through the gastrointestinal tract of non-ruminants largely unchanged, whereas the fiber in oats and bran are digested. The solubility of the structural carbohydrate component of the grain used in the invention can affect efficacy. In one form of the invention, the material will not dissolve in water. Many factors affect the efficacy of products used to control pests. Optimization of the attractiveness/palatability of the bait is critical in mollusc control. In this invention, continued feeding over a few days is all that is required to achieve optimal mollusc control.

The preferred embodiment of the invention comprises pellets formed of crushed corncobs, and a mollusc attractant such as molasses that also functions as a binder. Advantages of the invention are that the product can be safely used indoors, outdoors, in the home, around food and in the fields without fear of non-target toxicity. Application is possible by aerial vehicles such as airplanes and helicopters as well as conventional ground application technologies. The product can be dispensed by hand without fear of toxic chemical exposure. It is completely non-toxic to other animals, such as birds, cats, dogs, or reptiles that might eat a mollusc killed by the product. The product will not contaminate a drinking water supply, will not harm fish, birds or wild life, will not cause any harmful effects if swallowed or absorbed through the skin, will not harm children or pets, and can be safely eaten by domestic animals and livestock. In the preferred form of the invention, the product is applied as a pellet.

Cereal grains are generally milled to separate the floury endosperm from the bran and germ. The milled grain is then rolled to extract the oil from the germ. The remaining product is a non-nutritional by-product known in the industry as "spent grain." The spent grain is then passed through a drying process and aerated to achieve a moisture content ranging from about 1-10% (and preferentially about 7%-9%). The cellulose in a workable size particle is then mixed with the aforementioned attractant and binding substance and used as is, or pelletized to ranges of about ⅛-inch (3 mm) to about ⅜-inch (9 mm) inch in diameter. The product is dried to a moisture level of preferably about 7%-9%, which causes the product to be extremely hydrophilic. The attractant is selected according to mollusc preferences. Examples are molasses, beer, milk, blood, shrimp, digestible carbohydrates, nuts, fish, vegetable extracts, dry or liquid. The pellets may be used in both urban and rural settings, around buildings, including homes, in agricultural settings, such as barns, grain bins, and animal quarters.

DESCRIPTION OF A PREFERRED EMBODIMENT

One example of a preferred composition is produced by preparing a substantially dry base of a plant derived structural carbohydrates rich in cellulose and/or hemicellulose and/or lignin, such as crushed corncobs, without kernels, and 1% by weight of molasses as a mollusc attractant and binder. The kernels are first removed from the corncobs in a mill. The cores of the corncobs are then drilled to recover a powder used for other purposes. The remains of the cobs are then crushed to a various U.S. sieve sizes so as to be easily pelletized. The crushed corncobs are dried to a preferential moisture level of between about 7% and about 9% moisture, by weight. The dried particles are then mixed thoroughly with molasses. The mixture is formed into pellets in a pelletizing mill, such as a Scott Pellet Mill. The molasses acts both as a binder and a sweet attractant.

Additional materials may be added to further enhance the product efficacy at this time including without limitation: mineral and organic salts of metals (that increase the efficacy of the preparation by increasing mollusc mortality by introducing a second mode of mortality; namely metabolic poisons); anti-weathering agents (that increase the rain fastness of the product); colorants (that make the product less attractive to birds hence resulting in less non-target loss); pH stabilizers (that maintain the pH over the shelf life period of the product); preservatives (that prevent microbial spoilage); adjuvants (that increase the uptake and/or contact adhesion to the mollusc of the preparation); complexing agents (that increase uptake of the active materials in or on the mollusc); buffering agents (that maintain the preparation at the optimal pH); flow agents (that assist in the flowability of the material when dispensed by machine); anti-clumping agents (that reduce product to product adhesion); humectants (moisture retaining agents); and other hydrophilic polymers (water absorbing polymers that increase the water absorbing efficiency); inorganic acids (that act as buffering agents); organic acids (that act as buffering agents); inorganic salts (buffering agents); hydrophobic coating polymers (to protect the product from free moisture), wax coatings (anti-weathering agents), organic salts (buffering agents); clays (filling agents and flow agents); silica (irritant for molluscs); diamataceous earths (mollusc irritants); plant extracts (irritants, feeding enhancers, and toxicants); microbial agents (biological molluscicides), and combinations thereof. The pellets are distributed in locations where the molluscs are active. Over a period of several days, the molluscs die after consuming the pellets.

The material preparations used in this invention for mollusc control can be formed into shapes other than pellets. Further, other carbohydrates and/or proteins and/or fats and/or oils and/or attractants can be used, such as honey, chocolate, blood plasma, peanut butter, fish, beer, milk, synthetic colorings and flavorings, and other similar materials. The pellets may be coated with a paraffin or polymer coating to protect the composition from contact with water. The pellets are placed in areas where there is evidence of mollusc activity. The pellets are replenished as needed until signs of mollusc activity cease. For example, the common garden snail (*Helix aspersa* Muller) requires the use of about 2-4 oz. (50-100 grams) in piles in areas of maximum mollusc activity. Alternatively, the material can be broadcast at rates of 1-lb. per 100 to 1000 square feet (9 $M^2$ to 9.5 $M^2$).

The mortality inducing properties may be enhanced by adding such naturally occurring non-toxic substances as Kaolinite, gypsum, borates, diamataceous earth, and plant extracts. These materials will further enhance the mortality inducing properties of the preparation by providing a synergistic secondary mode of molluscicidal action. As with many natural products, when applied alone their efficacy is less than conventional poisons, in particular they tend to take longer to kill molluscs. However when two or more of these natural substances are combined with the subject of this invention the overall performance is improved. Materials such as pH stabilizers, colorants, preservatives, and anti-weathering agents, may be added to improve storability, provide for better rain fastness and maintain the product's constitution. Combining the materials with molluscopathogenic microbes, nematodes and/or, protozoans can further enhance the preparation by introducing a second mode of action to the preparation; in this case microbial molluscicides.

Example 1

Extracting

Procedure: Treatment groups of 20 wild collected common garden snails (size range 15 g to 50 g) were placed in a well aerated plastic container and maintained at 100% relative humidity. Total animal mass per replicate (20 animals) was adjusted at the beginning of the experiment to within 10% of each other. The animals were acclimatized for three days and fed ad libitum dandelion leaves during the period. After the third day, the garden snails were exposed to the following treatments by placing the preparations in their enclosure in quantities of 100 g. Bait was renewed every 5 days. Each treatment was replicated 5 times.
1. A preparation of crushed corncobs, pelletized to ⅛th inch, no attractants.
2. A preparation of crushed corncobs prepared to a coarse grind (crumb size+/−1-8 mm), no attractants.
3. Same preparation as 1 above, but with 0.5% iron sulfate incorporated into the preparation.
4. Same preparation as 1 above, but with 0.5% aluminum sulfate incorporated into the preparation.
5. Same preparation as 3 above, but with 0.1% citric acid incorporated into the preparation as a pH stabilizer.
6. Same preparation as 1 above, but with 10% gypsum added as a filling agent.
7. Same preparation as 5 above, but with 10% gypsum added as a filling agent
8. Same preparation as 4 above, but with 0.1% citric acid added as a pH stabilizer.
9. Conventional Molluscicide (metaldehyde).
10. A preparation of crushed corncobs, pelletized to ⅛th inch, with molasses added.
11. Control (fed dandelion leaves).
Experiment 1, conducted February 2003.
Results:

| Treatment | % Mort @ 3 days | % Mort. @ 5 days | % Mort @ 10 days | % Mort @ 15 days | % Mean wt loss @ death. |
| --- | --- | --- | --- | --- | --- |
| 1 | 0 | 5 | 60 | 70* | 15* |
| 2 | 0 | 6 | 70 | 75 | 18* |
| 3 | 0 | 0 | 85* | 95** | 7 |
| 4 | 0 | 5 | 90* | 90* | 8 |
| 5 | 0 | 0 | 85* | 90* | 7 |
| 6 | 0 | 0 | 65* | 90* | 17* |
| 7 | 0 | 0 | 55 | 60* | 12* |
| 8 | 10 | 15 | 90* | 100** | 8 |
| 9 | 0 | 20 | 80* | 100** | 4 |
| 10 | 0 | 0 | 75* | 95** | 24* |
| 11 | 0 | 0 | 10 | 10 | 3 |

*Significant result at P = 0.01,
**Significant result at P = 0.001 according to the standard students t-Test.
Value followed by the same symbol are not significantly different from one another.

Example 2

Procedure: Treatment groups of 25 wild collected common garden slugs (size range 3 g-7 g) were placed in a well aerated plastic container and maintained at 100% R.H. Total animal mass per replicate (20 animals) was adjusted at the beginning of the experiment to within 10% on each other. The animals were acclimatized for three days and fed ad libitum dandelion leaves during the period. After the third day, the garden slugs were exposed to the following treatments by placing the preparations in their enclosure in quantities of 100 g. Bait was renewed every 5 days. Each treatment was replicated 4 times.
1. A preparation of crushed corncobs, pelletized to ⅛th inch, no attractants.
2. Same preparation as 1 but with 0.5% iron sulfate incorporated into the preparation.
3. Same preparation as 1 but with 0.5% aluminum sulfate incorporated into the preparation.
4 Same preparation as 2 two but with 0.1% citric acid incorporated into the preparation as a pH stabilizer.
5. Same preparation as 1 but with 10% gypsum added as a filling agent.
6. Same preparation as 4 but with 10% gypsum added as a filling agent
7. Same preparation as 3 but with 0.1% citric acid added as a pH stabilizer.
8. Conventional Molluscicide (metaldehyde)
9. A preparation of crushed corncobs, pelletized to ⅛th inch, molasses added.
10. Control (fed Dandelion leaves).
Experiment 1 conducted April, 2003.
Results:

| Treatment | % Mort @ 3 days | % Mort. @ 5 days | % Mort @ 10 days | % Mort @ 15 days |
| --- | --- | --- | --- | --- |
| 1 | 0 | 25 | 45* | 70* |
| 2 | 0 | 30 | 80* | 95** |
| 3 | 0 | 15 | 90* | 90** |
| 4 | 0 | 10 | 100* | 100** |
| 5 | 0 | 30 | 55* | 80* |
| 6 | 0 | 40 | 55* | 65* |
| 7 | 10 | 45 | 90* | 100** |
| 8 | 0 | 25 | 80* | 100** |
| 9, | 0 | 45 | 75* | 95** |
| 10, | 0 | 0 | 10 | 10 |

*Significant result at P = 0.01,
**Significant result at P = 0.001 according to the standard student T-Test.
Value followed by the same symbol are not significantly different from one another.

Experiment 2 (repeat of experiment 1 in example 2), Conducted May, 2003

Results:

| Treatment | % Mort @ 3 days | % Mort. @ 5 days | % Mort @ 10 days | % Mort @ 15 days | % Mean wt loss @ death. |
|---|---|---|---|---|---|
| 1 | 0 | 0 | 25 | 60* | 9 |
| 2 | 0 | 0 | 15 | 95* | 10 |
| 3 | 0 | 0 | 40 | 90* | 18 |
| 4 | 0 | 0 | 45 | 90* | 11 |
| 5 | 0 | 0 | 20 | 90* | 14 |
| 6 | 0 | 0 | 60 | 60* | 21 |
| 7 | 0 | 0 | 35 | 85* | 23 |
| 8 | 0 | 0 | 45 | 80* | 14 |
| 9 | 0 | 0 | 65 | 75* | 14 |
| 10 | 0 | 0 | 0 | 0 | n/a |

*Significant result at P = 0.05 according to the Students T-test.
Value followed by the same symbol are not significantly different from one another.
Results: All treatments were comparable to the control levels achieved with a conventional molluscicide.

Example 3

Procedure

Plant derived structural carbohydrate sources were tested alone and in mixtures of varying proportions to assess the effects of these materials and mixtures on mollusc (garden snails) mortality. Treatments and replicates were standardized according to procedures in example 1. The materials were individually pulverized and then mixed together according to weight percentages. No additional materials were added. The preparations were dried to a level of 7%-9% moisture by weight and applied in the particulate form.

The Affect on Mollusc Mortality of Spent Grain and Other Sources Of Plant Derived Structural Carbohydrates Mixed With Corn Cob Percentage Mix

| Material | T1 | T2 | T3 | T4 | T5 | T6 | T7 | T8 | T9 |
|---|---|---|---|---|---|---|---|---|---|
| Corn Cob | 98 | 49 | 49 | 49 | 49 | 49 | 49 | 49 | 49 |
| Rye straw |  | 49 |  |  |  |  |  |  |  |
| Coir fiber |  |  | 49 |  |  |  |  |  |  |
| Cotton fiber |  |  |  | 49 |  |  |  |  |  |
| Wheat straw |  |  |  |  | 49 |  |  |  |  |
| Rice straw |  |  |  |  |  | 49 |  |  |  |
| Oats straw |  |  |  |  |  |  | 49 |  |  |
| Millet fiber |  |  |  |  |  |  |  | 49 |  |
| Barley straw |  |  |  |  |  |  |  |  | 49 |
| % Mortality at 1 week | 25 | 0 | 10 | 0 | 20 | 35 | 0 | 0 | 15 |
| % Mortality at 2 weeks | 80 | 55 | 45 | 35 | 30 | 75 | 55 | 40 | 20 |

An attractant was used in all treatments composed of 2% mixture of molasses and beer.

Example 4

Field tests of a preparation of crushed corncobs with the following additives:
1% molasses; 1% beer; 0.5% aluminum sulfate; 0.1% citric acid.

A naturally occurring population of garden snails and slugs were discovered in Reedley, Calif. on dandelions in a residential garden. The above mentioned preparation was placed on trays (10 trays, 100 g per tray) and observed for evidence of slug and snail feeding during the night. Counts were made on the feeding trays every third night.

Results:

| Mean number of Molluscs observed nightly on the feeding trays: | | | | |
|---|---|---|---|---|
|  | Day 3 | Day 10 | Day 15 | Day 20 |
| Slugs | 4 | 7 | 2 | 2 |
| Garden Snails | 5 | 4 | 3 | 0 |

The preparation appears to be highly palatable to common garden mollusc pests, and the results of these trials would indicate that the embodiment of this invention has the ability to control these molluscs.

It is to be understood that variations and modifications of the present invention may be made without departing from the scope thereof. It is also to be understood that the present invention is not to be limited by the specific embodiments disclosed herein.

What is claimed is:

1. A method for inducing death in molluscs comprising the steps of:
   exposing terrestrial molluscs to a material comprising at least about 49% corn cob and a structural carbohydrate selected from the group of hay, straw, seed husks, seed chaff, coconut coir fiber, sisal fiber, coconut shells, nut shells, cotton fibers, cereal seed chaff, legume seed pods, sugar cane bagasse and combinations thereof, wherein said material does not include a conventional chemical molluscicide, and does not include beet pulp; and
   inducing disruption of the physiology of the mollusc by ingestion of the material by the mollusc
   wherein the structural carbohydrate is mixed with a selection from the following group: molluscopathogenic microbes, molluscopathogenic nematodes, molluscopathogenic protozoans, and combinations thereof.

2. A method for disrupting natural metabolic processes in a terrestrial mollusc comprising the steps of exposing the mollusc to a material comprising
   a. at least about 49% corn cob,
   b. a mixture made up of a structural carbohydrate selected from the group consisting of hay, straw, seed husks, seed chaff, coconut coir fiber, sisal fiber, coconut shells, nut shells, cotton fibers, cereal seed chaff, legume seed pods, sugar cane bagasse and combinations thereof,
   c. a microbial agent, and
   d. an attractant,
   wherein said material does not include a conventional chemical molluscicide, and does not include beet pulp, and
   inducing disruption of the physiology of the mollusc by ingestion of the material by the mollusc.

3. The method of claim 2 wherein said microbial agent is a biological molluscicide.

4. The method of claim 2 wherein a pH stabilizer is added to said mixture.

5. The method of claim 4 wherein said pH stabilizer agent is selected from the group consisting of organic acid, inorganic acid, salt of organic acids, salt of inorganic acid, citric acid and its salts, malic acid and its salts, lactic acid and its salts, acetic acid and its salts, fumeric acid and its salts, and combinations thereof.

6. The method of claim 2 wherein a humectant is added to said mixture.

7. The method of claim 6 wherein said humectant is a moisture retaining agent.

8. The method of claim 2 wherein a hydrophilic polymer is added to said mixture.

9. The method of claim 8 wherein said hydrophilic polymer is selected from the group consisting of water absorbing polymers and combinations thereof.

10. The method of claim 2 wherein a colorant is added to said mixture.

11. The method of claim 10 and wherein said colorant is selected from the group consisting of natural and synthetic dyes.

12. The method of claim 2 wherein an adjuvant is added to said mixture.

13. The method of claim 12 wherein said adjuvant agent is selected from the group consisting of an anionic surfactant, a cationic surfactant, a non-ionic surfactant, a complexing agent, and combinations thereof.

14. The method of claim 2 wherein an anti-clumping agent is added to said mixture.

15. The method of claim 14 wherein said anti-clumping agent is selected from the group consisting of a clay, a talk, and combinations thereof.

16. The method of claim 2 further comprising a substance selected from the group consisting of kaolinite, gypsum, borates, diamataceous earth, silicates, plant extracts, and combinations thereof.

17. The method of claim 2 wherein an anti-weathering agent is added to said mixture.

18. The method of claim 17 wherein said anti-weathering agent is a hydrophobic polymer.

* * * * *